United States Patent
Yeh et al.

(10) Patent No.: US 8,026,271 B2
(45) Date of Patent: Sep. 27, 2011

(54) FORMULATIONS OF INDOL-3-YL-2-OXOACETAMIDE COMPOUNDS

(75) Inventors: Teng-Kuang Yeh, Bellevue, WA (US); Chiung-Tong Chen, Zhunan (TW); Yu-Sheng Chao, Warren, NJ (US)

(73) Assignee: National Health Research Institutes, Miaoli County (TW)

( * ) Notice: Subject to any disclaimer, the term of this patent is extended or adjusted under 35 U.S.C. 154(b) by 396 days.

(21) Appl. No.: 12/171,515

(22) Filed: Jul. 11, 2008

(65) Prior Publication Data

US 2010/0010059 A1 Jan. 14, 2010

(51) Int. Cl.
*A61K 31/404* (2006.01)
(52) U.S. Cl. .......................... 514/414; 514/415; 514/419
(58) Field of Classification Search .................. 514/414, 514/415, 419
See application file for complete search history.

(56) References Cited

U.S. PATENT DOCUMENTS

| | | | |
|---|---|---|---|
| 6,903,104 B2 | 6/2005 | Chen et al. | |
| 6,979,456 B1 | 12/2005 | Parikh et al. | |
| 2003/0181482 A1 | 9/2003 | Chen et al. | |
| 2006/0134204 A1* | 6/2006 | Wong et al. | 424/464 |
| 2007/0207173 A1 | 9/2007 | Chen | |
| 2008/0176946 A1* | 7/2008 | Ossovskaya et al. | 514/617 |
| 2009/0004262 A1* | 1/2009 | Shaw et al. | 424/456 |

OTHER PUBLICATIONS

Patterson, A.M. et al. "The Ring Index, 2nd Ed.", American Chemical Society, Columbus, Oh, 1960, Entry #2527, p. 326.*
Draetta, G. and Pagano, M. in "Annual Reports in Medicinal Chemistry, vol. 31", 1996, Academic Press, San Diego, p. 241-246.*
Sausville et al. Cancer Research, 2006, vol. 66, pp. 3351-3354.*
Johnson et al. British J. of Cancer, 2001, 84(10):1424-1431.*
Strickley, Pharmaceutical Research, 2004, vol. 21, No. 2, pp. 201-230.*
Torrado et al. International Journal of Pharmaceutics, 1997, vol. 156, pp. 181-187.*
Mu, L. and S.S. Feng, "Vitamin E TPGS Used as Emulsifier in the Solvent Evaporation/Extraction Technique for Fabrication of Polymeric Nanospheres for Controlled Release of Paclitaxel (Taxol)," Journal of Controlled Release 80:129-144 (2002).
Varma, Manthen V.S. and Ramesh Panchagnula, "Enhanced Oral Paclitaxel Absorption with Vitamin E-TPGS: Effect of Solubility and Permeability in Vitro, In Situ and In Vivo," European Journal of Pharmaceutical Sciences, 25:445-453 (2005).
Li et al., "Synthesis and Biological Evaluation of N-Heterocyclic Indolyl Glyoxylamides as Orally Active Anticancer Agents," J. Med. Chem., 46:1706-1715 (2003).
Khoo et al., "The Formulation of Halofantrine as either non-solubilising PEG 6000 or solubilising lipid based solid dispersions: Physical stability and absolute bioavailability assessment," International Journal of Pharmaceutics, 205:65-78 (2000).
Tang et al., "Development of Solid Self-Emulsifying Drug Delivery Systems: Preparation Techniques and Dosage Forms," Drug Discovery Today, 13(13/14): 606-612 (2008).

* cited by examiner

*Primary Examiner* — James Anderson
(74) *Attorney, Agent, or Firm* — Occhiuti Rohlicek & Tsao LLP

(57) ABSTRACT

This invention relates to an oral formulation containing an effective amount of the compound of the following formula I:

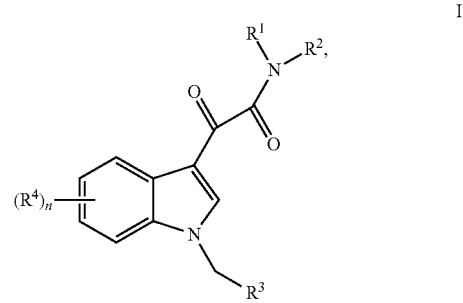

d-alpha-tocopheryl polyethylene glycol 1000 succinate ("TPGS"); and 2-(2-ethoxyethoxy)ethanol ("Transcutol"). $R^1$ through $R^4$ and n are defined herein. Also disclosed is a method of treating cancer by administering this formula to a subject orally.

16 Claims, No Drawings

FORMULATIONS OF INDOL-3-YL-2-OXOACETAMIDE COMPOUNDS

BACKGROUND OF THE INVENTION

Cancer is a leading cause of death in developed countries. Despite continuing advances in diagnosis and treatment regimens, most existing treatment methods have undesirable side effects and limited efficacy. Treatment of cancer is complicated by the variety of mechanisms involved in the formation and metastasis of tumors. Many of them are still not well understood. Chemotherapy is a major option for the first-line treatment in cancers such as leukemia and a second-line treatment for cancers such as refractory solid tumors.

Most current anticancer drugs are small molecule chemicals, which need to be administered into patients via a parenteral infusion. Clinical complications with the parenteral administrations have been documented and thus extra cares and cost for hospitalization are essential. Recent efforts in the discovery of anticancer drugs have been focused on finding oral composition containing active anticancer agents. N-(3-methylisothiazol-5-yl)-2-[1-(3-methylisoxazol-5-ylmethyl)-1H-indol-3-yl]-2-oxoacetamide and its analogues have been recently discovered as potent anticancer agents, as disclosed in U.S. Pat. No. 6,903,104, whose content is hereby incorporated by reference in its entirety.

SUMMARY

This invention is partially based on a discovery that an oral formulation containing N-(3-methylisothiazol-5-yl)-2-[1-(3-methylisoxazol-5-ylmethyl)-1H-indol-3-yl]-2-oxoacetamide unexpectedly enhances the oral bioavailability of the compound.

In one aspect, this invention features an anticancer formulation, which contains d-alpha-tocopheryl polyethylene glycol 1000 succinate ("TPGS"), 2-(2-ethoxyethoxy)ethanol ("Transcutol"); and an effective amount of a compound of formula I:

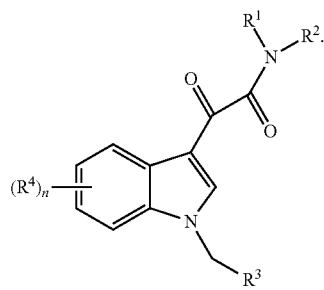

In this formula, $R^1$ is isoxazolyl, thiazolyl, isothiazolyl, 1,3,4-thiadiazolyl, 1,3-benzothiazolyl, quinolyl, isoquinolyl, thionaphthenyl, or benzofuranyl, each being optionally substituted with 1 to 6 independent $R^5$ groups; $R^2$ is H, C1-C10 alkyl, or aryl, each being optionally substituted with 1 to 4 independent $R^5$ groups; $R^3$ is C1-C10 alkyl, C2-C10 alkenyl, C2-C10 alkynyl, C3-C10 cycloalkyl, C4-C10 cycloalkenyl, isoxazolyl, furanyl, thiophenyl, thiazolyl, imidazolyl, pyridyl, or heterocyclyl, each being optionally substituted with 1 to 4 independent $R^5$ groups; each $R^4$ is independently H, $NO_2$, halo, CN, $R^7$, $OR^7$, $CO_2R^7$, $SR^7$, $NR^7R^7$, $C(O)R^7$, $C(O)NR^7R^7$, $OC(O)R^7$, $S(O)_2R^7$, $S(O)_2NR^7R^7$, $NR^7C(O)$ $NR^7R^7$, $NR^7C(O)R^7$, $NR^7(COOR^7)$, $NR^7S(O)_2NR^7R^7$, $NR^7S(O)_2R^7$, or $S(O)_2OR^7$; n is 0, 1, 2, 3, or 4; each $R^5$ is independently H, C1-C10 alkyl optionally substituted with 1 to 4 independent $R^6$ groups, C2-C10 alkenyl, C2-C10 alkynyl, C3-C10 cycloalkyl, aryl optionally substituted with 1 to 4 independent $R^6$ groups, heteroaryl optionally substituted with 1 to 4 independent $R^6$ groups, heterocyclyl optionally substituted with 1 to 4 independent $R^6$ groups, halo, haloalkyl, $SR^7$, $OR^7$, $NR^7R^7$, $COOR^7$, $NO_2$, CN, $C(O)R^7$, $C(O)NR^7R^7$, $OC(O)R^7$, $S(O)_2R^7$, $S(O)_2OR^7$, $S(O)_2NR^7R^7$, $NR^7C(O)NR^7R^7$, $NR^7C(O)R^7$, $NR^7(COOR^7)$, $NR^7S(O)_2$ $NR^7R^7$, or $NR^7S(O)_2R^7$; each $R^6$ is independently C1-C10 alkyl, C2-C10 alkenyl, C2-C10 alkynyl, halo, haloalkyl, CN, $NO_2$, $OR^7$, or $SO_2R^7$; each $R^7$ is independently H, C1-C10 alkyl, C2-C10 alkenyl, C2-C10 alkynyl, C3-C10 cycloalkyl, aryl, heteroaryl, or heterocyclyl, each optionally substituted with 1 to 4 independent $R^8$ groups; each $R^8$ is independently H, OH, $OR^9$, C1-C10 alkyl, halo, aryl, $NO_2$, or CN; and each $R^9$ is independently H, C1-C10 alkyl, or aryl; each being optionally substituted with 1 to 4 independent OH, halo, CN, $NO_2$, or $CO_2H$ groups. The formulation is administered orally.

The term "halo" refers to any radical of fluorine, chlorine, bromine or iodine. The terms "alkyl", "alkenyl" and "alkynyl" refer to hydrocarbon chains that can be straight-chain or branched-chain, containing the indicated number of carbon atoms. For example, C1-C10 indicates the group can have from 1 to 10 (inclusive) carbon atoms in it. The terms "ring" and "ring system" refer to a ring comprising the delineated number of atoms, said atoms being carbon or, where indicated, a heteroatom such as nitrogen, oxygen or sulfur. The ring itself, as well as any substituents thereon, can be attached at any atom that allows a stable compound to be formed.

The term "aryl" refers to a 6-carbon monocyclic or 10-carbon bicyclic aromatic ring system wherein 0, 1, 2 or 3 atoms of each ring can be substituted by a substituent. Examples of aryl groups include phenyl, naphthyl and the like.

The term "heteroaryl" refers to an aromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, wherein 0, 1, 2 or 3 atoms of each ring can be substituted by a substituent. Examples of heterocyclyl groups include piperazinyl, pyrrolidinyl, dioxanyl, morpholinyl, tetrahydrofuranyl, and the like.

The compounds described herein include the compounds themselves, as well as their salts, their solvates, and their prodrugs, if applicable. A salt, for example, can be formed between an anion and a positively charged group (e.g., amino) on a compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, mesylate, succinate, fumarate, tartrate, tosylate, salicylate, lactate, naphthalenesulfonate, and acetate. Likewise, a salt can also be formed between a cation and a negatively charged group (e.g., carboxylate) on a compound. Suitable cations include sodium ion, potassium ion, magnesium ion, calcium ion, and an ammonium cation such as tetramethylammonium ion. The compounds also include those salts containing quaternary nitrogen atoms. Examples of prodrugs include esters and other pharmaceutically acceptable derivatives, which, upon administration to a subject, are capable of providing active compounds described herein (see Goodman and Gilman's, The Pharmacological basis of Therapeutics, 8$^{th}$ ed., McGraw-Hill, Int. Ed. 1992, "Biotransformation of Drugs"). In addition, the compounds having asymmetric centers, can occur as racemates, racemic mixtures, single enantiomers, individual diastereomers, and diastereomeric mixtures.

In the formulation of this invention, the TPGS can be 10-80% (e.g., 70-80%) by weight and the Transcutol can be 20-60% (e.g., 20-30%) by weight. The formulation can further include polyethylene glycol ("PEG") having a molecular weight ranging from 300 to 6000 (e.g., from 400 to 1000). One example of the PEG used to practice this invention is PEG 400. In the formulation just described, the PEG can be 10-80% (e.g., 30-70% or 40-65%) by weight, the TPGS can be 10-80% (e.g., 10-50% or 15-40%) by weight, and the Transcutol can be 10-60% (e.g., 10-30% or 15-25%) by weight. The formulation of this invention can be encapsulated in a capsule (e.g., a soft or hard-shell capsule). The capsule can be formed of one or more polymers, such as collagen, gelatin, gum arabic, and polyethylene. The formulation of this invention can be free of glyceride (e.g., triglyceride, diglyceride, monoglyceride), fatty acid, and fatty acid esters (e.g., fatty acid esters of hydroxyalkanes or of dihydroxyalkanes) and derivatives thereof. The compound of formula I in the formulation can be N-(3-methylisothiazol-5-yl)-2-[1-(3-methylisoxazol-5-ylmethyl)-1H-indol-3-yl]-2-oxoacetamide.

In the formulation of this invention, the compound of formula I is the active ingredient. TPGS, Transcutol, or PEG described above, as a pharmaceutical acceptable carrier, is a substantially inactive ingredient in the formulation of this invention. The formulation can be in a liquid form at room temperature. The formulation can also be in the form of a semi-solid, e.g., a paste, or a wet solid at room temperature. For example, the liquid formulation described above can be further mixed with a solid excipient or carrier, such as powders of polyvinylpyrrolidone, preferably having molecular weight of about 2500 to about 50,000 (e.g., povidone, PVP-K30), which is used as an absorbent to reduce the likelihood of the liquid formulation leaking from the capsule. The molecular weight of a polymer described herein is either the number average molecular weight or the weight average molecular weight, depending upon different determining methods well known in the art. For example, the commercially available PEG 400 has a weight average molecular weight of 400.

In the formulation of this invention, other conventional ingredients can be added, e.g., anti-oxidants such as d-alpha-tocopherol, ascorbyl palmitate, butyl hydroxyl anisole (BHA), butyl hydroxyl toluene (BHT), and plasticizers such as propylene glycol.

In another aspect, this invention features a method of treating cancer by administering orally to a subject an effective amount of the above-described formulation. Examples of the cancer include, but are not limited to, a human leukemia, sarcoma, osteosarcoma, lymphoma, melanoma, ovarian, skin, testicular, gastric, pancreatic, renal, breast, prostate colorectal, head and neck, brain, esophageal, bladder, adrenal cortical, lung, bronchus, endometrial, cervical or hepatic cancer, or cancer of unknown primary site. The cancer can also be a cancer of a drug resistance phenotype of which the cancer cells express P-glycoprotein (MDR), multidrug resistance-associated proteins (MRP), lung cancer resistance-associated proteins (LRP), breast cancer resistance proteins (BCRP) or other proteins associated with resistance to anticancer drugs.

Also within the scope of this invention are use of the above-described formulation via oral administration to treat cancer and use of the above-described formulation for the manufacture of a medicament for treating cancer.

The details of one or more embodiments of the invention are set forth in the description below. Other features, objects, and advantages of the invention will be apparent from the description and from the claims.

DETAILED DESCRIPTION OF THE INVENTION

The compound of formula I used to practice this invention can be synthesized by conventional methods. In general, the compounds of the formulae described herein are conveniently obtained via standard organic chemistry synthesis methods, including those methods illustrated in the schemes and the examples (e.g., Example 1) herein.

As can be appreciated by the skilled artisan, the synthetic schemes herein are not intended to constitute a comprehensive list of all means by which the compounds described and claimed in this application can be synthesized. Further methods will be evident to those of ordinary skill in the art. Additionally, the various synthetic steps described above can be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2nd. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995); and subsequent editions thereof.

As an example, the compounds used to practice this invention are prepared according to the synthetic scheme shown below. Variables and groups in the chemical structural formulas in the methods below are defined as delineated herein for any of the formulae, including formula I.

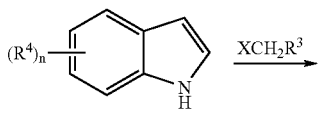

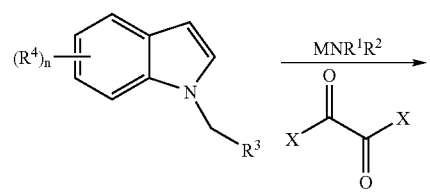

-continued

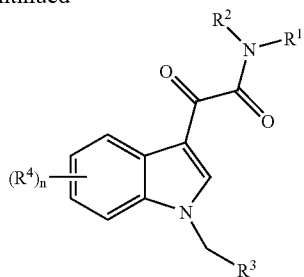

A solution of indolyl compound starting material in solvent (e.g., tetrahydrofuran, isopropanol, dichloromethane, dioxane, dimethyl formamide, dimethyl sulfoxide, or toluene) is reacted with a base (e.g., sodium hydride, potassium hydroxide, or potassium tert-butoxide) and a compound of the formula $XCH_2R^3$ (where X is a leaving group). The resulting intermediate is reacted with an oxalyl derivative and an amine of the formula $MNR^1R^2$ (where M is H or metal cation, e.g., K, Li, Na), to give compounds of the formulae delineated herein. The desired compounds or intermediates can be isolated and purified using standard synthetic techniques or can be reacted further (i.e., "one-pot synthesis") without isolation or purification.

Alternatively, the compounds used to practice this invention are prepared according to the following synthetic scheme shown below:

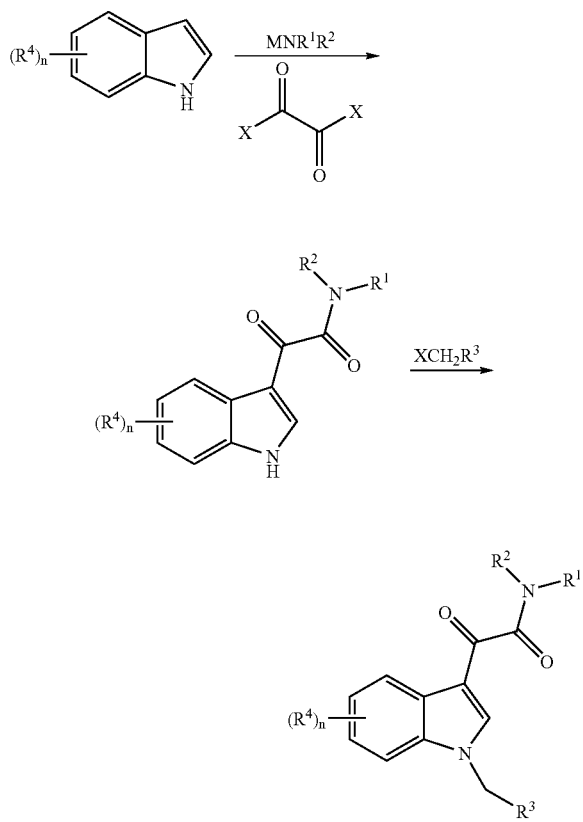

The indolyl starting material is dissolved in solvent (e.g., diethyl ether, tetrahydrofuran, or dichloromethane) and reacted with an oxalyl derivative (e.g., oxalyl chloride) and an amine of the formula $MNR^1R^2$ (where M is H or metal cation, e.g., K, Li, Na). The intermediate compound is reacted with a compound of the formula $XCH_2R^3$ (where X is a leaving group) to give compounds of the formulae herein. The desired compounds or intermediates can be isolated (and optionally purified) or can be reacted further (i.e., "one-pot synthesis" without isolation or purification).

The compound thus synthesized can be further purified by flash column chromatography, high performance liquid chromatography, crystallization, or any other suitable methods.

To prepare the formulation of this invention, one can simply mix the compound of formula I, the TPGS, the Transcutol, and optionally the PEG at the desired ratio in any sequence. For example, one can mix a predetermined amount of the compound with Transcutol and optionally PEG at a predetermined concentration, and then add TPGS. Mixing can be achieved by shaking, agitation, or swirling and is controlled to reconstitute the active ingredient(s) (e.g., the compound of formula I) into the inactive ingredient(s) (e.g., TPGS, Transcutol, and PEG). The formulation may be prepared at room temperature or heated at a temperature between 40 and 80° C. to facilitate the mixing process. At any stage of the preparation, sterilization, e.g., by an autoclave, may be applied.

The formulation of this invention may further contain one or more solid excipients minimize leakage of the liquid mixture from the capsule. The solid excipients can be included in the formulation at any stage of its preparation. The suitable concentration of a solid excipient in the formulation for conferring the intended effect, as recognized by those skilled in the art, can be assayed using conventional methods.

The formulation of this invention, when administered orally to a subject in need thereof, is preferably encapsulated in a capsule (e.g., a soft or hard-shell capsule). The capsule can be formed of a material that is well recognized by one skilled in the art, for example, porcine collagen, bovine collagen material, gelatin (e.g., porcine gelatin), gum arabic, pectin, poly(ethylene-co-maleic anhydride), poly(vinylmethylether-co-maleic anhydride), carrageenan, and agar-agar.

One can employ the formulation of this invention to treat cancer by administering orally to a subject in need of the treatment an effective amount of the formulation.

As used herein, the term "treating" or "treatment" is defined as the administration of an effective amount of the formulation to a subject, who has cancer, a symptom of the cancer, a disease or disorder secondary to the cancer, or a predisposition toward the cancer, with the purpose to cure, alleviate, relieve, remedy, or ameliorate the cancer, the symptom of, the disease or disorder secondary to, or the predisposition toward the cancer.

The term "an effective amount" refers to an amount of a compound of formula I in the formulation or an amount of the formulation which confers a therapeutic effect on the treated subject. The therapeutic effect may be objective (i.e., measurable by some test or marker) or subjective (i.e., subject gives an indication of or feels and effect). An effective amount of the compound described above may range from about 0.1 mg/Kg to about 500 mg/Kg body weight per day, alternatively from about 1 to about 50 mg/Kg body weight per day.

The formulation of this invention may be administered from 1 to 6 times per day (e.g., at 0.1 mg-100 mg/dose). The amount of active ingredient that can be combined with the carrier materials to produce a single dosage form may vary depending upon the host treated. A typical formulation of this invention will contain from 0.5% to 20% of an active compound (w/w).

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

EXAMPLE 1

Synthesis of N-(3-methylisothiazol-5-yl)-2-[1-(3-methylisoxazol-5-ylmethyl)-1H-indol-3-yl]-2-oxoacetamide ("BPR0C261")

A solution of indole (1.17 g, 10 mmol) in 10 mL tetrahydrofuran was added dropwise to a suspension of potassium tert-butoxide (1.34 g, 12 mmol) in 10 mL tetrahydrofuran. The reaction mixture was stirred at room temperature for 2 hours, then 5-(chloromethyl)-3-methylisoxazole (1.32 g, 10 mmol) in 5 mL tetrahydrofuran was added dropwise. The solution was allowed stand for 4 hours and then 10 mL saturated ammonium chloride was added with stirring. The mixture was extracted three times with a total of 60 mL of ether, the organic phase was dried using anhydrous magnesium sulfate and filtered, and the filtrate was concentrated in vacuum and purified by flash chromatography on silica gel. The eluent used was a mixture of n-hexane and ethyl acetate in the ratio 8:1 (vol/vol). Yield: 1.61 g, 76%.

A solution of 5-(1H-1-indolylmethyl)-3-methylisoxazole (212 mg, 1.0 mmol) in 10 mL diethyl ether was added to oxalyl chloride (254 mg, 2.0 mmol) dropwise at 0° C. The reaction mixture was stirred at 0° C. for 3 hours and then the reaction solvent was evaporated. The residue was dissolved in 5 mL tetrahydrofuran and then the 3-methyl-5-isothiazolamine (114 mg, 1.0 mmol) and triethylamine (1 mL) in 10 mL tetrahydrofuran was added dropwise. The mixture was stirred for 10 hours and then 1 N NaOH (4 mL) was added to the reaction flask dropwise. The mixture was extracted three times with a total of 60 mL of tetrahydrofuran, the organic phase was dried using anhydrous magnesium sulfate and filtered, and the filtrate was concentrated in vacuum. The residue was crystallized from methanol. Yield: 0.27 g, 71%.

NMR: 10.33 (s, 1H), 9.15 (s, 1H), 8.44 (d, J=6.3 Hz, 1H), 7.45-7.38 (m, 3H), 6.82 (s, 1H), 5.96 (s, 1H), 5.48 (s, 2H), 2.49 (s, 3H), 2.52 (s, 3H).

MS (M+1): 381.1.

EXAMPLE 2

Preparation of a Formulation of BPR0C261 in TPGS, Transcutol, and PEG

BPR0C261 (5 mg) was first dissolved in Transcutol (99 mg). Then PEG 400 (330 mg) was added to the solution. TPGS (105 mg) was heated at 60-70° C. until it was molten. The molten TPGS was then added to the Transcutol/PEG solution with constant stirring to form a homogenous solution. The solution was further stirred at 40° C. until it became a clear solution.

EXAMPLE 3

Solubility of BPR0C261 in Different Carriers

The solubility of BPR0C261 in different drug carriers or mixed carriers was evaluated. The solubility is defined as the maximum amount of a compound dissolved in a carrier or mixed carrier at room temperature. The results are shown in Table 1 below.

TABLE 1

| | Carrier or mixed carrier | Solubility (mg/mL) |
|---|---|---|
| 1 | Double distilled water ("DDW") | ~$1.2 \times 10^{-4}$ |
| 2 | DMSO[a] | ~5 |
| 3 | DMSO (20%[b]), Tween 80 (10%), and DDW (70%) | <5 |
| 4 | Ethanol (3%), Glycerol (2%), PEG 400 (70%), PG (20%), and Transcutol (5%) | ~10-30 |
| 5 | Glycerol (5%) and PEG 400 (95%) | ~10-30 |
| 6 | TPGS (20%) and PEG 400 (80%) | ~10-30 |
| 7 | Transcutol (10%) and PEG 400 (90%) | ~10-30 |
| 8 | DMSO (10%), PEG 400 (80%), and propylene glycol (10%) | ~10-30 |
| 9 | Transcutol (10%), Cremophor EL (20%), and PEG 400 (70%) | ~10-30 |
| 10 | TPGS (20%), Transcutol (20%), and PEG 400 (60%) | ~50 |
| 11 | TPGS (40%), Transcutol (20%), and PEG 400 (40%) | ~50 |
| 12 | TPGS (75%) and Transcutol (25%) | ~50 |
| 13 | DMSO (5%), Cremophor EL (25%), and DDW (70%) | <5 |
| 14 | Methylcellulose (1%), Tween 80 (2%), PEG 400 (10%), and DDW (87%) | <1 |

[a]dimethyl sulfoxide
[b]all of the percentages listed in this table were calculated based on a ratio of the initial volume of each individual carrier component to the sum of initial volumes of all components.

EXAMPLE 4

Oral Bioavailability of BPR0C261

The oral bioavailability of BPR0C261 was assessed by comparing the pharmacokinetic ("PK") profiles obtained from orally administered ("po") BPR0C261 in various oral formulation described herein with the PK profile obtained from intravenously administered ("IV") BPR0C261.

An intravenous formulation of BPR0C261 (carriers: 5% DMSO, 25% Cremophor EL, and 70% water, v/v/v) was administered intravenously by a bolus injection to a group of three mice each via the tail vein, in a single dose of 2 mg/Kg body weight. A blood sample (0.15 mL) was drawn at different points (pre-dose, 2 min, 5 min, 15 min, 30 min. 1 hr, 2 hr, 4 hr, 6 hr, 8 hr, and 24 hr after dosing) from each animal via the cardiac puncture and stored in ice (0-5° C.).

An oral formulation of BPR0C261 (i.e., the just-described formulation containing DMSO, Cremophor EL, and water, or a formulation containing TPGS, Transcutol, and optionally PEG 400), was orally administered in various doses to groups of three mice by gavage. A blood sample (0.15 mL) was drawn at different points (pre-dose, 15 min, 30 min. 1 hr, 2 hr, 4 hr, 6 hr, 8 hr, and 24 hr after dosing) from each animal via the cardiac puncture and stored in ice (0-5° C.).

Plasma was separated from the blood sample by centrifugation at 15,000 g for 15 min at 4° C. The separated plasma was then stored in a freezer (−20° C.). All plasma samples were analyzed for the BPR0C261 concentrations by HPLC-Tandem Mass spectrometry.

BPR0C261 plasma concentration data were used to obtain the PK profile for the IV or po administration, i.e., a plasma-concentration vs. time curve. The area under the curve ("AUC") was then calculated. Oral bioavailability (F %) was determined by comparing the dose-normalized area under the curve for the oral formulation ("$AUC_{po}/dose_{po}$") with that for the intravenous formulation ("$AUC_{IV}/dose_{IV}$"), i.e., F%= $[AUC_{po}/dose_{po}]/[AUC_{IV}/dose_{IV}]$.

The oral bioavailability of BPR0C261 in the formulation containing 5% DMSO, 25% Cremophor EL, and 70% water (v/v/v) was determined to be 18% in mouse. Unexpectedly, the oral bioavailability of BPR0C261 in formulations containing TPGS, Transcutol, and optionally PEG 400 was determined to be in a range of 25% to 80%.

OTHER EMBODIMENTS

All of the features disclosed in this specification may be combined in any combination. An alternative feature serving the same, equivalent, or similar purpose may replace each feature disclosed in this specification. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A pharmaceutical formulation comprising:
   15-80% by weight d-alpha-tocopheryl polyethylene glycol 1000 succinate ("TPGS");
   20-30% by weight 2-(2-ethoxyethoxy)ethanol ("Transcutol"); and
   N-(3-methylisothiazol-5-yl)-2-[1-(3-methylisoxazol-5-ylmethyl)-1H-indol-3-yl]-2-oxoacetamide.

2. The formulation of claim 1, wherein the TPGS is 70-80% by weight.

3. The formulation of claim 1, further comprising polyethylene glycol ("PEG") having a molecular weight ranging from 300 to 6000.

4. The formulation of claim 3, wherein the PEG has a molecular weight ranging from 400 to 1000.

5. The formulation of claim 3, wherein the PEG is 10-65% by weight.

6. The formulation of claim 5, wherein the PEG is 30-65% by weight and the TPGS is 15-50% by weight.

7. The formulation of claim 6, wherein the PEG is 40-65% by weight, the TPGS is 15-40% by weight, and the Transcutol is 20-25% by weight.

8. The formulation of claim 1, wherein the formulation is encapsulated in a capsule.

9. The formulation of claim 8, wherein the capsule is formed of at least one polymer selected from the group consisting of porcine collagen material, bovine collagen material, gelatin, gum arabic, pectin, poly(ethylene-co-maleic anhydride), poly(vinvlmethylether-co-maleic anhydride), carrageenan, and agar-agar.

10. The formulation of claim 1, wherein the formulation is free of glyceride, fatty acid, and fatty acid ester.

11. The formulation of claim 10, wherein the TPGS is 70-80% by weight.

12. The formulation of claim 10, further comprising polyethylene glycol (PEG) having a molecular weight ranging from 300 to 6000.

13. The formulation of claim 12, wherein the PEG has a molecular weight ranging from 400 to 1000.

14. The formulation of claim 13, wherein the PEG is 10-65% by weight.

15. The formulation of claim 14, wherein the PEG is 40-65% by weight, the TPGS is 15-40% by weight, and the Transcutol is 20-25% by weight.

16. A method for treating cancer, the method comprising administering orally to a subject in need thereof an effective amount of the formulation of claim 1, wherein the cancer is leukemia, colorectal, nasopharyngeal, lung, or cervical cancer.

* * * * *